(12) United States Patent
Dahmen

(10) Patent No.: US 9,625,700 B2
(45) Date of Patent: Apr. 18, 2017

(54) VISUAL FIELD APPARATUS AND IMAGE TRANSMISSION APPARATUS FOR AN ENDOSCOPE

(75) Inventor: Jan Dahmen, Seitlingen-Oberflacht (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1024 days.

(21) Appl. No.: 13/151,004

(22) Filed: Jun. 1, 2011

(65) Prior Publication Data
US 2011/0292195 A1    Dec. 1, 2011

(30) Foreign Application Priority Data
Jun. 1, 2010    (DE) .................. 10 2010 022 430

(51) Int. Cl.
*A61B 1/06* (2006.01)
*G02B 23/24* (2006.01)
(Continued)

(52) U.S. Cl.
CPC ........ *G02B 23/243* (2013.01); *A61B 1/00096* (2013.01); *A61B 1/00135* (2013.01);
(Continued)

(58) Field of Classification Search
CPC ............ A61B 1/00096; A61B 1/00135; A61B 1/00179; A61B 1/00183; A61B 1/00188; G02B 23/243; G02B 23/2469
(Continued)

(56) References Cited

U.S. PATENT DOCUMENTS 4,878,485 A * 11/1989 Adair ................. A61B 1/00101
600/122
4,974,580 A * 12/1990 Anapliotis .................... 600/122
(Continued)

FOREIGN PATENT DOCUMENTS

DE    4238977 A1 *  5/1994
DE    4410821 A1 *  4/1996
(Continued)

OTHER PUBLICATIONS

Henning, Machine generated translation of WO 2004/004303, Jan. 2004.*
(Continued)

*Primary Examiner* — David Harvey
(74) *Attorney, Agent, or Firm* — Whitmyer IP Group LLC

(57) ABSTRACT

A visual field apparatus for an image transmission apparatus including a channel that connects the proximal end and the distal end of the visual field apparatus, for inputting the image transmission apparatus, and an optical device on the distal end of the channel that is configured to influence the visual field or the focusing of the image transmission apparatus. A method for preparing an endoscope for a succeeding use including determining a visual field required for the succeeding use, selecting a visual field apparatus with the determined visual field and a channel, and combining the image transmission apparatus with the selected visual field apparatus. A method for autoclaving a visual field apparatus for an image transmission apparatus, including closing the channel on the proximal end so that it is fluid-tight, autoclaving the visual field apparatus after the fluid-tight closing, and opening the channel on the proximal end after autoclaving.

13 Claims, 7 Drawing Sheets

(51) Int. Cl.
  *A61B 1/00* (2006.01)
  *A61B 1/07* (2006.01)
(52) U.S. Cl.
  CPC ...... *A61B 1/00179* (2013.01); *A61B 1/00183* (2013.01); *A61B 1/00188* (2013.01); *A61B 1/07* (2013.01); *G02B 23/2469* (2013.01); *G02B 23/2484* (2013.01)
(58) Field of Classification Search
  USPC .................................................. 348/65, 68
  See application file for complete search history.

(56) References Cited

U.S. PATENT DOCUMENTS

| | | | | |
|---|---|---|---|---|
| 4,979,498 A | * | 12/1990 | Oneda | A61B 1/00142 600/118 |
| 5,051,824 A | | 9/1991 | Nishigaki | |
| 5,188,094 A | * | 2/1993 | Adair | A61B 1/00142 348/E5.027 |
| 5,301,061 A | * | 4/1994 | Nakada et al. | 359/362 |
| 5,349,941 A | * | 9/1994 | Hori | A61B 1/00105 600/122 |
| 5,359,991 A | * | 11/1994 | Takahashi et al. | 600/122 |
| 5,368,014 A | * | 11/1994 | Anapliotis et al. | 600/112 |
| 5,496,259 A | * | 3/1996 | Perkins | A61B 1/05 600/121 |
| 5,556,367 A | * | 9/1996 | Yabe | A61B 1/00096 600/121 |
| 5,584,793 A | * | 12/1996 | Sauer | A61B 1/00101 206/370 |
| 5,599,278 A | * | 2/1997 | Hibbard | 600/133 |
| 5,609,561 A | * | 3/1997 | Uehara | A61B 1/042 348/75 |
| 5,621,830 A | * | 4/1997 | Lucey et al. | 385/25 |
| 5,690,605 A | * | 11/1997 | Hamlin | A61B 1/00142 600/109 |
| 5,704,892 A | * | 1/1998 | Adair | A61B 1/00073 600/121 |
| 5,817,015 A | * | 10/1998 | Adair | A61B 1/00101 600/121 |
| 5,863,287 A | * | 1/1999 | Segawa | A61B 1/00142 600/121 |
| 5,868,667 A | * | 2/1999 | Lin et al. | 600/133 |
| 5,879,367 A | * | 3/1999 | Yoshihashi | 600/160 |
| 6,007,484 A | * | 12/1999 | Thompson | A61B 1/00096 600/122 |
| 6,126,592 A | * | 10/2000 | Proch et al. | 600/114 |
| 6,174,280 B1 | * | 1/2001 | Oneda | A61B 1/00078 600/114 |
| 6,390,972 B1 | * | 5/2002 | Speier | A61B 1/042 348/73 |
| 6,478,730 B1 | * | 11/2002 | Bala | A61B 1/00142 600/121 |
| 6,478,731 B2 | * | 11/2002 | Speier et al. | 600/125 |
| 6,589,165 B2 | * | 7/2003 | Bodor et al. | 600/172 |
| D537,858 S | * | 3/2007 | Griffin | 396/27 |
| 7,410,462 B2 | * | 8/2008 | Navok | A61B 1/0011 600/131 |
| 7,426,339 B2 | * | 9/2008 | Takanashi | G03B 17/08 206/316.2 |
| 8,512,231 B2 | * | 8/2013 | Yamane | 600/170 |
| 8,569,713 B2 | * | 10/2013 | Evers | G21G 1/0005 250/428 |
| 2002/0013510 A1 | * | 1/2002 | Moriyama | A61B 1/125 600/118 |
| 2002/0013513 A1 | * | 1/2002 | Bala | 600/178 |
| 2002/0072653 A1 | * | 6/2002 | Ishizuka | A61B 1/00068 600/133 |
| 2002/0103420 A1 | * | 8/2002 | Coleman et al. | 600/173 |
| 2002/0128539 A1 | * | 9/2002 | Higuma et al. | 600/133 |
| 2005/0256377 A1 | * | 11/2005 | Deppmeier | A61B 1/002 600/176 |
| 2005/0283048 A1 | * | 12/2005 | Gill | A61B 1/00059 600/121 |
| 2007/0185383 A1 | * | 8/2007 | Mulhern | A61B 1/00142 600/121 |
| 2007/0197873 A1 | * | 8/2007 | Birnkrant | A61B 1/00016 600/160 |
| 2007/0208364 A1 | * | 9/2007 | Smith | A61B 1/00078 606/191 |
| 2008/0208191 A1 | * | 8/2008 | Kadykowski | A61B 17/00008 606/46 |
| 2008/0275303 A1 | * | 11/2008 | Koitabashi | A61B 1/0052 600/146 |
| 2009/0264706 A1 | | 10/2009 | Bala | |
| 2010/0292532 A1 | * | 11/2010 | Kadykowski | A61B 17/32 600/104 |
| 2012/0071721 A1 | * | 3/2012 | Remijan et al. | 600/121 |
| 2012/0220822 A1 | * | 8/2012 | Chen | A61B 1/00048 600/109 |

FOREIGN PATENT DOCUMENTS

| | | | |
|---|---|---|---|
| DE | 19511443 A1 | * | 10/1996 |
| DE | 102006017683 B3 | | 8/2007 |
| EP | 0842633 A1 | * | 5/1998 |
| JP | 09-269534 | * | 10/1997 |
| JP | 2004305586 A | * | 11/2004 |
| JP | 02008291951 A | * | 12/2008 |
| WO | PCT/US94/06033 | * | 12/1994 |
| WO | WO 2004/004303 A2 | * | 1/2004 |

OTHER PUBLICATIONS

Fiegert et al, Machine generated translation of DE4238977A1, May 1994.*
Schaller, Machine generated translation of DE19511443A1, Oct. 1996.*
German Search Report; Application No. DE 10 2010 022 430.8; Feb. 7, 2011; 4 pages.
European Search Report; Application No. EP 11 16 7891; Issued: Sep. 6, 2011; 6 pages.

* cited by examiner

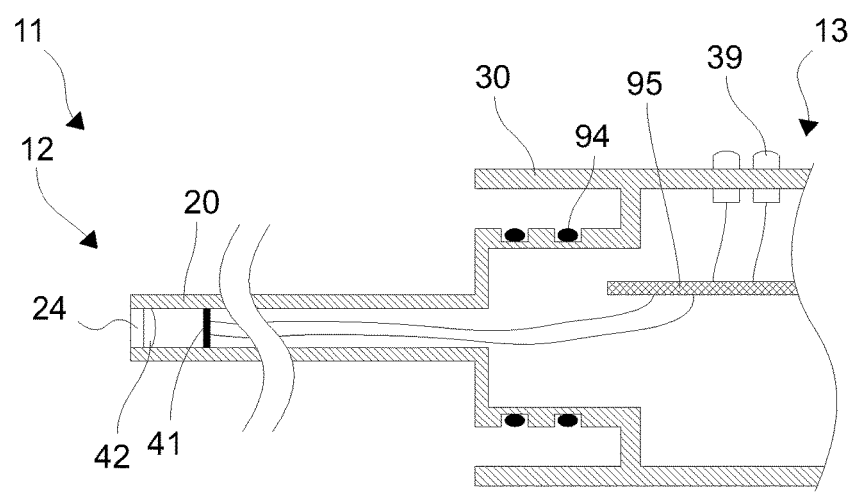
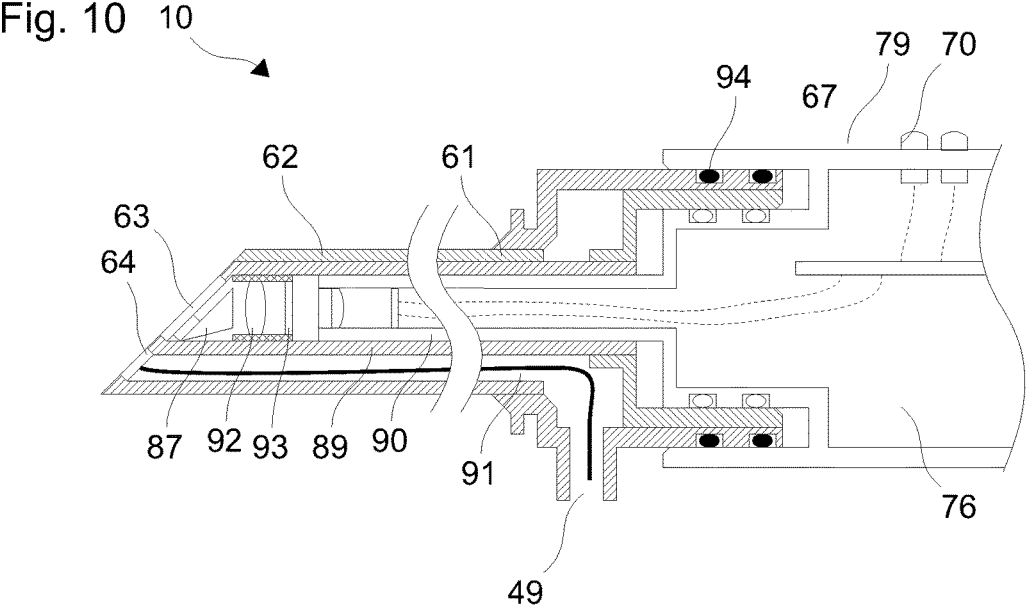

VISUAL FIELD APPARATUS AND IMAGE TRANSMISSION APPARATUS FOR AN ENDOSCOPE

CROSS-REFERENCE TO RELATED APPLICATIONS

The present application claims priority of German patent application No. 10 2010 022 430.8 filed on Jun. 1, 2010.

FIELD OF THE INVENTION

The present invention relates to a visual field apparatus for an image transmission apparatus, in particular for an endoscope, to an image transmission apparatus, an endoscope and a method for preparing an endoscope and for autoclaving a visual field apparatus.

BACKGROUND OF THE INVENTION

The visual field of an endoscope is the spatial area that is recorded by the stationary endoscope or can be recorded by the stationary endoscope. The visual field can be characterized by the spatial angle occupied by the recorded area with reference to the distal end of the endoscope, by the viewing direction and by the angular distance of opposite boundaries of the visual field. The viewing direction is the direction with respect to the distal end of the endoscope in which objects are located that are in the center of the recorded image during observation by the endoscope or are imaged on the center of a light-sensitive sensor or image sensor.

Different uses or applications of an endoscope, in particular different medical uses, require various visual fields as a rule, in particular different viewing directions and different sizes of the visual fields. A great number of varying endoscopes therefore exists, with different viewing directions and different sizes of the visual fields. Accordingly, different types of endoscope are kept available in hospitals, medical practices, and other medical installations. Acquisition, maintenance, and readiness of numerous diverse endoscopes—with several units of each type, as a rule—generate considerable costs as a result.

SUMMARY OF THE INVENTION

It is an object of the present invention to reduce the expense for acquisition and maintenance of endoscopes with numerous different visual fields.

This object is achieved through the contents of the independent claims.

Refinements are indicated in the dependent claims.

Some embodiments of the present invention are based on the idea of providing a visual field apparatus for an image transmission apparatus, in particular for an endoscope, that includes a channel that links the proximal and distal ends of the visual field apparatus and serves as an intake for the image transmission apparatus, and an optical device on the distal end of the channel that is configured at least to influence either the visual field or the focusing of the image transmission apparatus.

The reference to influencing the visual field of the image transmission apparatus does not signify merely cutting off part of the visual field without changing the position and size of the image of an object. Influencing the visual field, instead, means simultaneously modifying the size and/or displacing the position of the image of a particular object. For example, a pane of glass or a window or a glass covering with parallel level or else parallel curved border surfaces influences the visual field only insignificantly or not at all.

With one and the same image transmission apparatus, alternatively, it is possible now to combine various visual field apparatuses in order to form endoscopes with different visual fields. A greater number of different visual field apparatuses can be procured and kept in readiness at reasonable cost because of their comparatively simple structure. Every image transmission apparatus can be combined with several different visual field apparatuses.

In the event of damage or soiling of the visual field apparatus, it can easily be replaced and the image transmission apparatus can continue to be used. In particular, the visual field apparatus can be replaced and, for example, autoclaved after each medical use. The image transmission apparatus can also be easily replaceable, allowing it to be exchanged, for example in case of a defect, by a new image transmission apparatus, or to be replaced with an image transmission apparatus with different spectral properties.

The number of image transmission apparatuses that are to be kept in readiness is thereby drastically reduced. Even when the costs for producing or procuring the individual image transmission apparatuses are in the same order of magnitude as those for a conventional endoscope, the total costs can be drastically reduced if the production costs of the visual field apparatuses are markedly lower than those for a complete endoscope, because the number of required image transmission apparatuses is clearly smaller than the number of conventionally required endoscopes.

The optical device on the distal end of the channel, alternatively or in addition to the visual field, can influence the focusing of the image transmission apparatus. Objects that are sharply imaged by the image transmission apparatus onto a given image surface are in one surface. This surface, depending on the optical device, can be flat or domed, symmetrical or asymmetrical to the optical axis of the optical device. Influencing the focusing means, in particular, influencing or modifying the location and/or shape of this surface.

The optical device of the visual field apparatus is configured, in particular, at least either to refract or to reflect or to bend light. In particular, the optical device includes at least either a prism or a mirror or lens. With these relatively simple components, the visual field apparatus can be producible at reasonable cost.

The optical device of the visual field apparatus is configured, in particular, to change the direction of the illuminating and/or imaging beam path or to modify the divergence of light in the illuminating and/or imaging beam path.

The channel of the visual field apparatus can be configured to allow rotation of an image transmission apparatus around its longitudinal axis in the channel. In particular, the cross-sections of the image transmission apparatus and of the channel are adapted to one another for this purpose. For example, by means of circular cross-sections with corresponding radii, it is possible to guide the image transmission apparatus in the channel with little free play and simultaneously low friction, as well as to rotate and axially slide the image transmission apparatus in the channel. Consequently, in rotating the visual field apparatus around the longitudinal axis and correspondingly varying the viewing direction on a conical mantle while simultaneously securing the image transmission apparatus, it is possible to prevent tipping of the image. The endoscope composed of the visual field apparatus and image transmission apparatus thus can always provide an upright image regardless of the viewing direction.

Rotatability of the image transmission apparatus in the channel of the visual field apparatus means, in particular, that it can rotate by more than just a small angle, for example by at least 90 degrees, at least 180 degrees, at least 270 degrees, at least 360 degrees or any desired angle.

If the visual field apparatus includes a lens or other optically effective component, the focusing can be modified or the sharply imaged plane can be displaced by axially sliding the image transmission apparatus in the channel of the visual field apparatus. This simple type of focusing allows the use of a lens apparatus with a large aperture that generates a correspondingly bright and low-noise image. In comparison with a small aperture, as is often used conventionally, with correspondingly high depth of field and without focusing, the described focusing allows brighter and lower-noise images and/or of the use of lower illumination intensities.

If, in addition, a light-sensitive sensor of the image transmission apparatus—possibly together with a rod lens system—can be slid with respect to a lens, object lens or an optically effective component on the distal end of the image transmission apparatus, then at least either the focus or the focal length or size of the visual field can be modified. For a modification of the focal length, for example, at least a first lens or a first part of an object lens is coupled with the visual field apparatus and at least a second lens or a second part of an object lens is coupled with the image transmission apparatus.

Alternatively, the visual field apparatus can be employed with an image transmission apparatus that comprises an eyepiece or a coupling to the junction of a video camera on the proximal end instead of an image transmission apparatus. To transmit an image from the distal end to the proximal end of the image transmission apparatus, a rod lens system can be provided, as in the example described above. Alternatively, for example, an arranged bundle of lightwave conductors can be provided to transmit the image to the eyepiece or to the coupling. Foregoing comments on modifying the focus and/or focal length by sliding the visual field apparatus and the image transmission apparatus relative to one another also apply correspondingly for an image transmission apparatus with an eyepiece or a coupling.

The visual field apparatus can comprise an adjustment device to adjustably lock the position of an image transmission apparatus in the longitudinal direction in the channel. The adjustment device includes, for example, an adjustment screw, which can be positioned in the form of a sleeve or adjusting nut coaxially in the area of the shaft or in the area of an operating device of the image transmission apparatus. Such an adjustment device can make possible a fine adjustment, which is simultaneously easily performed and precise, of the focus or position of the sharply imaged plane.

The visual field apparatus can include one or more lightwave conductors to transmit illuminating light from the proximal end to the distal end of the visual field apparatus to illuminate an object that is to be observed. If the visual field apparatus includes several lightwave conductors to transmit illuminating light, said conductors in particular form an arranged bundle, contrary to an arranged bundle of lightwave conductors suitable for transmitting an image and used in many cases.

In addition, the visual field apparatus on the distal end can include a light outlet device to conduct illuminating light into an area outside the visual field apparatus. Said light outlet device can include an illuminating window and/or a prism and/or a lens and/or a mirror. Said light outlet device can be coupled with the distal end by one or more lightwave conductors integrated into the visual field apparatus to transmit illuminating light. Alternatively, the light outlet device can be configured to couple with one or more lightwave conductors integrated into an image transmission apparatus to transmit illuminating light.

The light outlet device integrated into the visual field apparatus or combined with one or more lightwave conductors integrated into the visual field apparatus to transmit illuminating light allows a substantial or complete adaptation of the illuminated area to the visual field.

The optical device on the distal end of the channel of the visual field apparatus can be insulated against liquids from outside or from the distal direction. For this purpose, a fluid-tight inserted covering glass or a fluid-tight connection can be provided between the optical device itself or the outermost distal element of the optical device on the one hand, and, for example, tubular structures of the visual field apparatus on the other hand. In addition, a fluid-tight insulation of the optical device can be provided from the proximal side or the channel. For this purpose, a fluid-tight inserted additional covering glass or a fluid-tight connection, for example, is provided between the optical device itself or an outermost proximal element of the optical device on the one hand and the inside wall of the channel on the other hand.

The fluid-tight insulation of the optical device allows an autoclaving of the visual field apparatus without penetration of moisture into the optical device. The optical properties of the optical device can thus be maintained without restriction even after multiple autoclaving cycles. If the optical device is not insulated against fluids from the proximal direction or the channel, then during autoclaving it is possible to insert a sealing stopper on the proximal end of the channel to avoid penetration of moisture into the channel and into the optical device. Such a sealing stopper can include one or more O-rings or other insulating devices.

The visual field apparatus can comprise a shaft, which can be as long as the shaft of the image transmission apparatus or even shorter than it. The visual field apparatus can be configured as a closed, in particular a fluid-tight, sleeve for the image transmission apparatus. In this case the visual field apparatus can make autoclaving of the image transmission apparatus between two uses superfluous. This can also be achieved if the visual field apparatus, if not surrounding the image transmission apparatus in the form of a sleeve completely and fluid-tight, instead is supplemented by a sterile cloth to cover parts of the image transmission apparatus that are not covered or encased by the visual field apparatus.

The visual field apparatuses described here can be configured for rigid or flexible image transmission apparatuses, in particular for video endoscopes, endoscopes with rod lens systems or with an arranged bundle of lightwave conductors for transmitting an image from the distal to the proximal area. The visual field apparatus can be configured correspondingly as rigid or flexible for this purpose. The described visual field apparatuses are configured in particular for use with medical endoscopes or are configured to be combined with an image transmission apparatus to form a medical endoscope. For this purpose the described visual field apparatuses are in particular autoclavable or sterilizable by other means or else configured as disposable articles or one-way articles at correspondingly low production costs.

The described visual field apparatuses, however, can also be configured for non-medical technical applications or for use with non-medical technical endoscopes or boroscopes. Because of the described visual field apparatuses, it is possible simultaneously to avoid soiling or else damage to an image transmission apparatus, in particular an endoscope, so that said apparatus can continue to be used immediately after exchanging the visual field apparatus without the need for previous expensive cleaning.

Each of the described visual field apparatuses can be configured for an image transmission apparatus that is an endoscope with all characteristics, properties and functionalities of an endoscope in the conventional sense of the term. Such an image transmission apparatus, even without one of the described visual field apparatuses, can be used as an endoscope in medical or non-medical technical endoscopic investigations or procedures. For this purpose the image transmission apparatus is, for example, autoclavable, comprises keys or other elements for operation by a user, and delivers a sharp image of objects.

Alternatively, each of the described visual field apparatuses can be configured for an image transmission apparatus that, only in combination with the visual field apparatus, comprises all properties and functions required for use in medical or non-medical technical endoscopic investigations or procedures. For example, the image transmission apparatus is not autoclavable or does not deliver a sharp image when it is not combined with a visual field apparatus.

Additional embodiments of the present invention are based on the idea of providing an image transmission apparatus with a shaft and at least either a device for optical transmission of an image from a distal end to a proximal end of the shaft or an image sensor for converting an optical image into an image signal, where the shaft is configured to be inserted into a channel in a visual field apparatus that on the distal end of the channel comprises an optical device, which influences the visual field of the endoscope. The image transmission apparatus is configured in particular to generate a sharp image of an object or only to generate such an image when the image transmission apparatus is inserted into a channel of one of the visual field apparatuses described above. The image transmission apparatus can comprise on the distal end of the shaft a fluid-tight inserted transparent closing, in particular a covering glass or an observation window of a transparent material.

Additional embodiments of the present invention are based on the idea of providing an endoscope with one of the visual field apparatuses described above and an image transmission apparatus that can be inserted into the channel of the visual field apparatus, in particular the image transmission apparatus described above, where the image transmission apparatus comprises at least either a device for optical transmission of an image from a distal end of the endoscope to a proximal end of the endoscope or an image sensor to convert an optical image into an image signal.

Additional embodiments of the present invention are based on the idea, in a method for providing an endoscope, of determining, for a succeeding use of the endoscope, a visual field that is required in the succeeding use, to select a visual field apparatus with the determined visual field, and to combine an image transmission apparatus with the selected visual field apparatus, in particular to insert it into a channel of the selected visual field apparatus in order to form an endoscope.

Additional embodiments of the present invention are based on the idea, in a method for autoclaving a visual field apparatus for an image transmission apparatus, with a channel that connects the proximal end and the distal end of the visual field apparatus, for intake of an image transmission apparatus, and an optical device on the distal end of the channel that is configured to influence the visual field of the endoscope, to close off the channel at the proximal end in fluid-tight manner, after fluid-tight closing to autoclave the visual field apparatus and after autoclaving to open up the channel on the proximal end.

The methods described above are performed in particular with one of the visual field apparatuses described above and/or with the image transmission apparatus described above. The visual field apparatuses described above and the image transmission apparatuses described above are configured and suited in particular for performing one of the methods cited above.

BRIEF DESCRIPTION OF THE DRAWINGS

Embodiments are described in greater detail hereinafter with reference to the appended drawings, which are as follows.

FIG. 9 is a schematic depiction of an image transmission apparatus.

FIG. 10 is a schematic depiction of a visual field apparatus for an image transmission apparatus.

DETAILED DESCRIPTION OF THE INVENTION

Each of FIGS. 1 through 10 shows a schematic depiction of an endoscope or of components of an endoscope or of the assembly of components of an endoscope. At the same time, each of FIGS. 1 through 10 shows essentially a depiction of a section along a plane that contains a longitudinal axis of the endoscope. The depiction of lightwave conductors or electrical lines can depart from a pure sectional depiction in order to clarify the spatial arrangement of the same. The endoscope or components of the endoscope can be partly or entirely rotationally symmetrical to the longitudinal axis of the endoscope.

In each of FIGS. 1 through 10, an image transmission apparatus or at least parts of an image transmission apparatus are depicted. For purposes of a transparent depiction, however, components and characteristics of the image transmission apparatuses are partly provided with reference numbers only in FIGS. 1, 5, 7 and 9. In FIGS. 2, 6, 8 and 10, many components and characteristics of the image transmission apparatuses are not provided with reference numbers in order to avoid overloading the illustrations.

Figure 1:
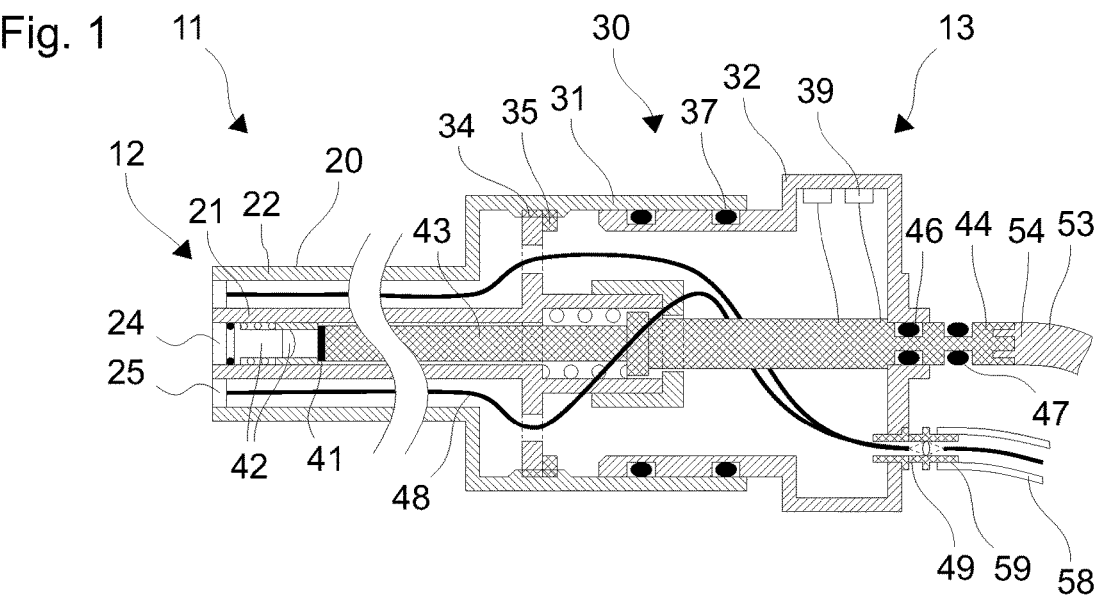
FIG. 1 is a schematic depiction of an image transmission apparatus.

FIG. 1 shows an image transmission apparatus 11. The image transmission apparatus 11 can be an endoscope with all characteristics and properties—in particular, performance characteristics and functionalities—of an endoscope in the conventional sense of the term. In particular, the image transmission apparatus can be configured and suited for use in medical or non-medical technical endoscopic investigations or procedures without a visual field apparatus as it is described hereinafter with reference to the other illustrations. For this purpose the image transmission apparatus is, for example, autoclavable, comprises keys or other elements for operation by a user, and supplies a sharp image of objects.

Alternatively, the image transmission apparatus 11 can be configured so that, only in combination with a visual field apparatus as it is described hereinafter with reference to the other illustrations, it comprises all the properties and functions required for use in medical or non-medical technical endoscopic investigations or procedures. For example, the image transmission apparatus 11 is not autoclavable or does not supply a sharp image if it is not combined with a visual field apparatus.

The image transmission apparatus 11 comprises a distal end 12 and a proximal end 13. A shaft 20 of the image transmission apparatus 11 comprises an inner tube 21 and an outer tube 22. On the distal end 12 the shaft 20 comprises an observation window 24 and one or more illuminating windows 25, which each is made of glass or another transparent material. The observation window 24 and the illuminating window 25 are, in particular, optically separated from one another, for example by a distal edge of the inner tube 21. Alternatively, a single window is provided that assumes the functions of the observation window 24 and of the illuminating window or windows 25.

On the proximal end 13 the image transmission apparatus 11 comprises a handling device 30 with a distal housing part 31 and a proximal housing part 32. The distal housing part 31 of the handling device 30 is mechanically connected, in particular joined, with the proximal end of the outer tube 22 of the shaft 20. The proximal end of the inner tube 21 is also mechanically connected with the distal housing part 31 of the handling device 30, in this example by a screwing device 34 with a lock nut 35.

The distal housing part 31 and the proximal housing part 32 of the handling device 30 can rotate relative to one another with respect to the longitudinal axis of the image transmission apparatus 11 and in particular of the shaft 20 and/or can be slid axially. Between the distal housing part 31 and the proximal housing part 32 of the handling device 30, one or more O-rings 37 are provided for fluid-tight insulation of the interior of the handling device 30 and of the shaft 20 on the one hand, and with respect to the outside on the other hand.

On the handling device 30, in particular on the distal housing part 32 of the handling device 30, it is possible to provide switches, keys or other operating elements with which to control, for example, the illumination, recording of images or their storage. For example, magnetic sensors 39, shown in FIG. 1, are connected with the sensor carrier 43 via electric lines and with the plug-in connection 44 via said carrier.

On the distal end of the shaft 20, a light-sensitive sensor 41 and an object lens 42 are positioned in the inner tube 21. The object lens 42 images objects close to the distal end 12 of the image transmission apparatus 11 on the light-sensitive sensor 41. The light-sensitive sensor 41 is positioned on the distal end of a sensor carrier 43, which extends in rod shape in the inner tube 21 of the shaft 20 and farther all the way to the proximal end of the proximal housing part 32 of the handling device 30. The sensor carrier 43, as shown in FIG. 1, is pressed by a spring against the proximal end of the proximal housing part 32 of the handling device 30, where it supports itself. Alternatively, the sensor carrier 43 is fastened on the proximal end of the proximal housing part 32 of the handling device 30.

One or more electrical or optical signal lines in or on the sensor carrier 43 couple the light-sensitive sensor 41 with a plug-in connection 44 on the proximal end of the handling device 30. An O-ring 46 is provided for fluid-tight insulation between the sensor carrier 43 and the proximal housing part 32 of the handling device 30. An additional O-ring 47 is provided for fluid-tight insulation between the sensor carrier 43 and a visual field apparatus that is described subsequently with reference to FIG. 2.

Lightwave conductors 48 are positioned between the inner tube 21 and the outer tube 22 of the shaft 20 of the image transmission apparatus 11. The lightwave conductors 48 extend from the illuminating window or windows 25 all the way to a passageway or a plug-in connection 49 on the proximal end of the proximal housing part 32 of the handling device 30. Instead of the illuminating window 25 inserted as a transparent component, the distal ends of the lightwave conductors 48 can simply be cemented on the distal end of the shaft 20 of the image transmission apparatus 11 by means of an (optionally transparent) cement. By grinding and polishing the distal front surface of the shaft 20 with the ends of the lightwave conductors 48 and the cement, an optically high-caliber light outlet surface can be produced.

A signal cable 53 with a plug-in connection 54 can be connected with the plug-in connection 44 on the proximal end of the sensor carrier 43. It is possible, for example, for the signal cable 42 to replace electrical signals and electrical power between the light-sensitive sensor 41 and a device not shown in FIG. 1 for preparing and depicting images.

A lightwave conductor cable 58 with a plug-in connection 59 can be coupled with the passageway or the plug-in connection 49. Light from an external light source, not shown in FIG. 1, can be conducted to the distal end 12 of the image transmission apparatus 11 by the lightwave conductor cable 58, the plug-in connections 49, 59 and the lightwave conductors 48, in order to illuminate objects close to the distal end 12 of the image transmission apparatus 11.

The image transmission apparatus 11 described with reference to FIG. 1 comprises, as mentioned, a light-sensitive sensor 41, which converts light intensities present on its light-sensitive surface into analog or digital electrical or else optical signals. These signals constitute the image generated by the object lens 42 on the light-sensitive surface of the light-sensitive sensor 41 in analog or digital form. The signals are transmitted by the aforementioned electrical lines or by optical lightwave conductors in the sensor carrier to the proximal end 13 of the image transmission apparatus and further by the signal cable 53 to the apparatuses, not shown in FIG. 1, for evaluating signals and depicting the image (for example on a screen).

Alternatively, the image transmission apparatus 11 comprises a rod lens system, an arranged bundle of lightwave conductors or other optical device for transmitting the image generated by the object lens to the proximal end 13 of the image transmission apparatus 11. The image can then be observed on the proximal end 13 of the image transmission apparatus 11, for example by an eyepiece, can be converted into analog or digital electrical or else optical signals by a light-sensitive sensor, or can be transmitted further by an arranged bundle of lightwave conductors.

As mentioned, the image transmission apparatus 11 can be configured and suited to be used as an endoscope independently of the visual field apparatus described below with reference to FIG. 2. For this purpose, in particular the light-sensitive sensor 41 and the object lens 42 are configured and suited to capture, without further devices for refracting or reflecting light, a sharp image of an object close to the distal end 12 of the image transmission apparatus 11.

Alternatively, the image transmission apparatus 11 is configured to be used as an endoscope only in combination with the visual field apparatus described below with reference to FIG. 2. For this purpose, in particular the light-sensitive sensor 41 and the object lens 42 are configured and suited to capture a sharp image of an object close to the distal end 12 of the image transmission apparatus 11 only in combination with an additional device for refracting or reflecting light on the visual field apparatus described below. In addition, in this case the object lens 42 can be dispensed with.

Figure 2:
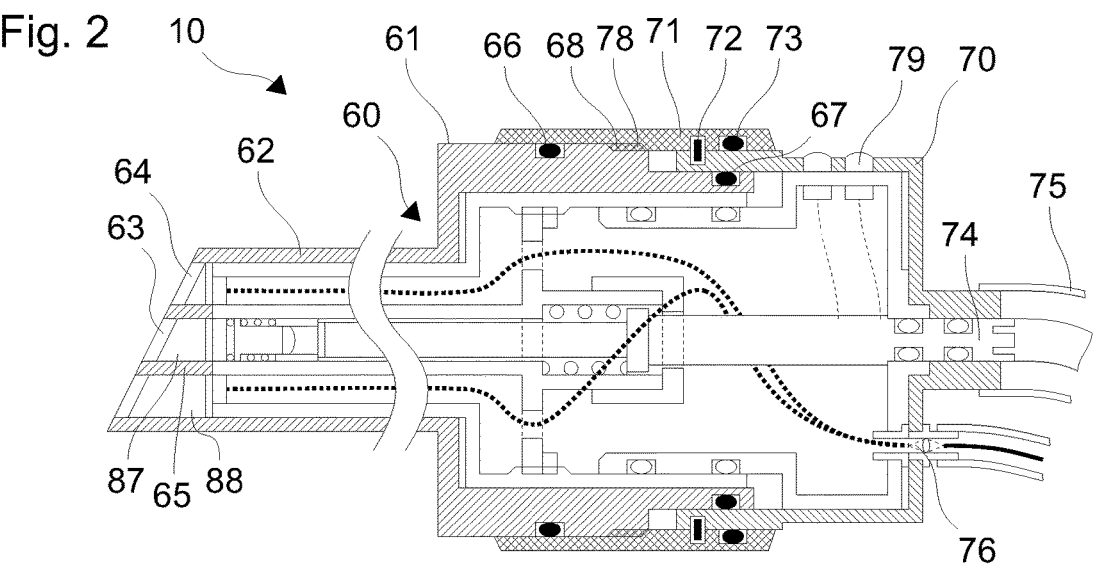
FIG. 2 is a schematic depiction of a visual field apparatus for an image transmission apparatus.

FIG. 2 shows a schematic depiction of a sleeve 60 from a visual field apparatus 61 and a proximal sleeve part 70 for the image transmission apparatus 11 described above with reference to FIG. 1. The visual field apparatus 61 is configured here simultaneously as a distal sleeve part, which forms the sleeve 60 together with the proximal sleeve part 70. Independently of whether the image transmission apparatus 11 can be used as an endoscope even without the visual field apparatus 61, the image transmission apparatus 11 and visual field apparatus 61 together form an endoscope 10.

The visual field apparatus 61 includes a shaft 62 with an observation window 63 and an illuminating window 64 on the distal end. The observation window 63 and illuminating window 64 are adapted in arrangement, size and shape to the observation window 24 or illumination window 25 on the distal end 12 of the shaft 20 of the image transmission apparatus 11. The observation window 63 and illuminating window 64 are optically separated from one another, for example by a frame 65 made of metal or other non-transparent material around the observation window 63. Alternatively, a single window is provided that assumes the functions of the observation window 63 and of the illuminating window or windows 64. In this case it can be useful or necessary to reduce scattered light, for example by blackening the window on a boundary between the two areas that assume the functions of the illuminating window 64 and observation window 63. O-rings 66, 67 and a thread 68 are provided on the visual field apparatus 61; their function is described hereinafter.

On the proximal sleeve part 70, a sleeve 71 is provided that is rotatably connected with the proximal sleeve part 70 by an axial fastening 72. The axial fastening 72 includes, for example, an open or closed ring, which engages in ring-shaped grooves on the proximal sleeve part 70 and on the sleeve 71. The axial fastening 72 allows rotation of the sleeve 71 relative to the proximal sleeve part 70, but prevents a relative axial sliding. In addition the sleeve 71 includes an O-ring 73 for fluid-tight insulation between the proximal sleeve part 70 and the sleeve 71.

The proximal sleeve part 70 includes on the proximal end an aperture 74 for intake of the proximal end of the sensor carrier 43 and of the plug-in connection 44. In addition, the proximal end of the proximal sleeve part 70 can be configured to provide a fluid-tight connection with a mantle 75 of the data cable 53 or with a mantle 75 for the data cable 53.

In addition, the proximal sleeve part 70 comprises an aperture 76 or a window through which the lightwave conductor cable 58 can be optically coupled with the lightwave conductors 48.

Configured on the sleeve 71 is a counter-thread 78 to the thread 68 on the visual field apparatus 61. The thread 68 on the visual field apparatus 61 and the counter-thread 78 on the sleeve 71 can be screwed to one another to provide a separable mechanical connection between the visual field apparatus 61 and the proximal sleeve part 70 via the sleeve 71 and the axial fastening 72. In addition, by means of the reciprocal engagement of the thread 68 on the visual field apparatus 61 and of the counter-thread 78 on the sleeve 71, a relative rotation of the sleeve 71 with respect to the visual field apparatus 61 is converted into an axial sliding of the same and thus a relative axial sliding of the visual field apparatus 61 and of the proximal sleeve part 70.

In addition, the proximal sleeve part 70 comprises keys 79, which are positioned opposite the magnetic sensors 39 and contain magnets. The keys 79 are configured in such a way that pressure or force on a key 79 causes a movement of a magnet positioned inside it, said movement being recorded by the magnetic sensor 39 opposite. The keys comprise, for example, an elastic material and are insulated to be fluid-tight and, in particular, sterile. Alternatively to the keys 79 and magnetic sensors 39, other devices can be provided as user interfaces.

Proximally from the observation window 63, a prism 87 is positioned in the observation beam path on the visual field apparatus 61. Proximally from the illuminating window or windows 64, one or more prisms 88 are positioned in the illuminating beam path. The prisms 87, 88 can each be configured as a single piece along with the observation window 63 or the illuminating window 64. The prisms 87, 88 divert light by refraction and/or reflection to surfaces (especially by total reflection), thus modifying its direction. Thus the prisms 87, 88 influence the visual field and/or the recorded area of the endoscope 10 made up of the image transmission apparatus 11 and visual field apparatus or sleeve 60. As described hereinafter in greater detail with reference to FIGS. 3 and 4, it is thus possible, with one and the same image transmission apparatus 11 in combinations with different visual field apparatuses 61, to produce different visual fields that are distinguished from one another by their direction and size.

The sleeve 60, consisting of the visual field apparatus 61 and proximal sleeve part 70 with the sleeve 71, is configured in such a way that its inner surface is contiguous with the outer surface of the image transmission apparatus 11 or else is only at a small distance from it. In addition, the visual field apparatus 61, the proximal sleeve part 70 and the endoscope 11 are configured in such a way that a relative axial sliding of the visual field apparatus 61 and of the proximal sleeve part 70 causes a corresponding relative axial sliding of the distal housing part 31 and of the proximal housing part 32 of the operating device 30 of the image transmission apparatus 11. A relative axial sliding of the visual field apparatus 61 and of the sleeve part 70—for example, caused by a relative rotation of the sleeve 71 with respect to the visual field apparatus 61—can thus, for example, cause a displacement of the focus or arrangement of the light-sensitive sensor 41 relative to the object lens 42.

In addition, the visual field apparatus 61 and the proximal sleeve part 70 can be configured in such a way that a rotation of the visual field apparatus 61 is transmitted to the distal housing part 31 of the handling device 30 and to the shaft 20 and/or that a rotation of the proximal sleeve part 70 is transmitted to the proximal housing part 32 of the handling device 30. For this purpose, the visual field apparatus 61, proximal sleeve part 70 and housing parts 31, 32 of the handling device 30 comprise, for example, grooves and studs or other rigid or elastic catch-locking, mutually engaging details, which are not shown in the illustrations. Thus, for example, it is possible to modify a viewing direction of the endoscope 10 by rotating the proximal sleeve part 70 on the one hand with respect to the visual field apparatus 61 and sleeve 71 on the other hand.

The O-rings 66, 67, 73 on the visual field apparatus 61, on the proximal sleeve part 70 and on the sleeve 71 and the O-ring 47 on the image transmission apparatus 11 provide a fluid-tight insulation of the sleeve 60. In particular, the O-rings 66, 67, 73, 47 prevent penetration of non-sterile, liquid, gaseous or solid material into the sleeve 60 or the release of non-sterile material from the sleeve 60. After each use of the endoscope 10 with the image transmission apparatus 11 and the sleeve 60 in a medical procedure, it is therefore necessary only to sterilize, in particular to autoclave, the sleeve 60. The image transmission apparatus 11 itself must not be exposed to the thermal and mechanical impact of autoclaving. This functionality of the sleeve 60 made up of the visual field apparatus 61 and proximal sleeve part 70 is an optional functionality.

The frame 65, which surrounds the observation window 63 for optical insulation, with the sleeve as described above with reference to FIG. 2, widens here in tubular form. The proximal edge of the frame 65, when the image transmission apparatus 11 is inserted into the sleeve 60, is configured to be contiguous and optically close to the distal edge of the inner tube 21 of the shaft 20 of the image transmission apparatus 11 and to prevent or reduce the coupling of illuminating light into the observation beam path.

In the image transmission apparatus presented above with reference to FIG. 1 and the sleeve presented above with reference to FIG. 2, the viewing direction and visual field are already pre-established by the image transmission apparatus. In the image transmission apparatus 11 shown in FIG. 3 and the sleeve 60 shown in FIG. 4, a viewing direction that departs from the longitudinal axis of the image transmission apparatus 11 and a visual field that is not symmetrical with this longitudinal axis are generated only by the sleeve 60, in particular the prisms 87, 88. The materials and geometries of the prisms 87, 88 determine the angle between the viewing direction and the longitudinal axis and the position of the visual field or of the area that is illuminated by the lightwave conductors 48 and through the illuminating windows 25, 64 and recorded by the light-sensitive sensor 41 by means of the object lens 42, observation windows 24, 63 and the prism 87.

If the visual field apparatus 61 with the observation window 63, illuminating window or windows 64 and the prisms 87, 88 can rotate with respect to the image transmission apparatus 11 around its longitudinal axis, then by rotating the visual field apparatus 61 and simultaneously fixing the image transmission apparatus 11 (for example by the proximal sleeve part 70), the viewing direction of the endoscope 10 on a conical mantle can be modified without causing the recorded image to be tipped.

Figure 3:
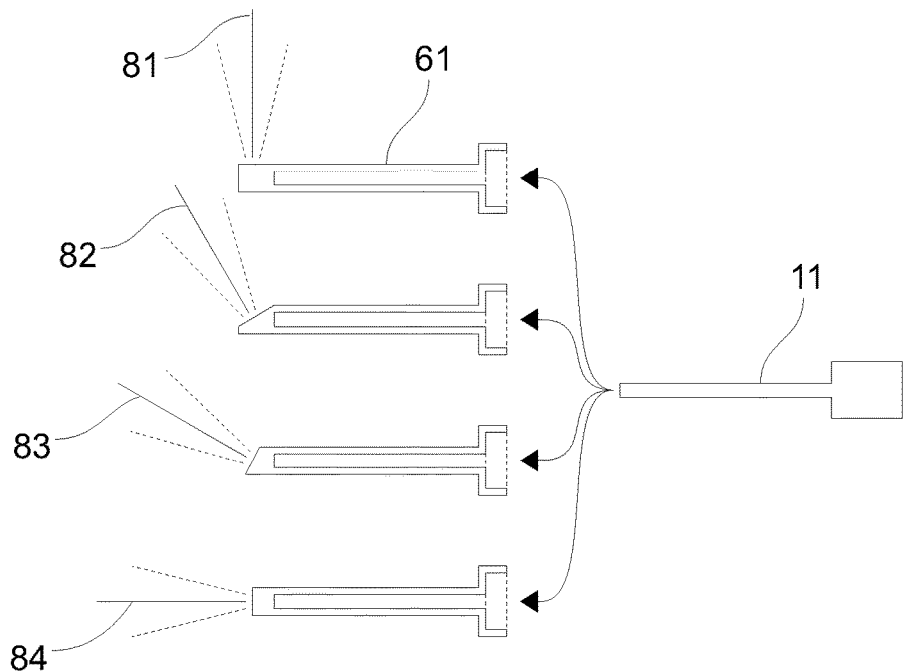
FIG. 3 is a schematic depiction of a combination of an image transmission apparatus with one of several visual field apparatuses.
Figure 4:
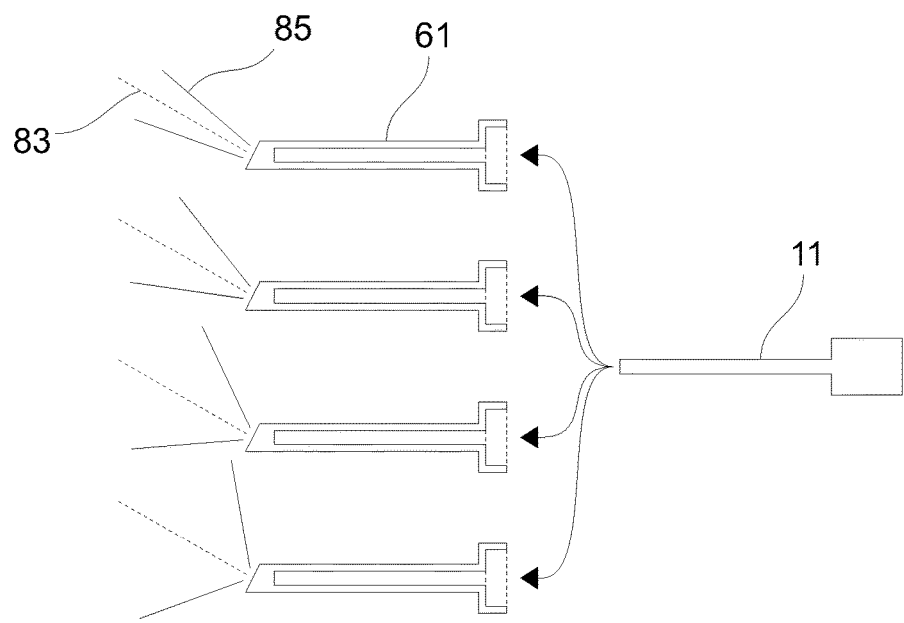
FIG. 4 is a schematic depiction of a combination of an image transmission apparatus with one of several visual field apparatuses.

FIGS. 3 and 4 show schematic depictions of the alternative combination of an image transmission apparatus 11 with various visual field apparatuses 61 to produce various visual fields. FIG. 3 shows various visual field apparatuses 61, which in combination with the image transmission apparatus 11 result in various viewing directions 81, 82, 83, 84 with an angle to the longitudinal axis of the image transmission apparatus 11 and of the visual field apparatus 61 of approximately 90 degrees, approximately 60 degrees, approximately 30 degrees and approximately zero degrees. Angles of 15 degrees, 45 degrees, 75 degrees or other angles, or any angle that can be selected within an angle interval, can be produced using corresponding visual field apparatuses.

FIG. 4 shows various visual field apparatuses 61, which in combination with an image transmission apparatus 11 at essentially the same viewing direction 83 produce visual fields of various size or angles of various size between opposite boundaries 85 of the visual fields. This combinational ability is also true of the image transmission apparatuses and visual field apparatuses described hereinafter with reference to FIGS. 5 through 10.

Figure 5:
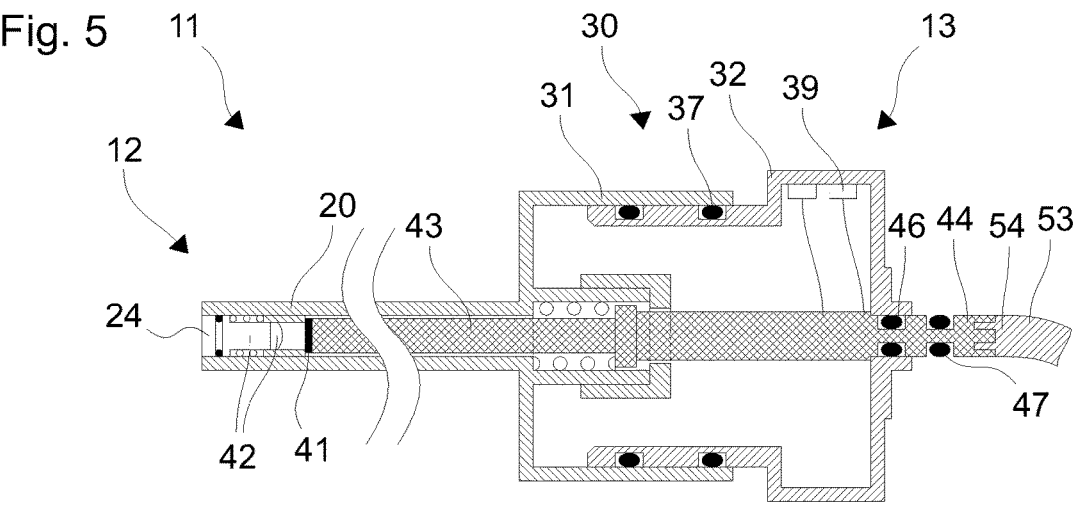
FIG. 5 is a schematic depiction of an image transmission apparatus.

FIG. 5 shows a schematic depiction of an image transmission apparatus 11, similar to the image transmission apparatus described above with reference to FIG. 1. Similarly as in the image transmission apparatus described above with reference to FIG. 1, in the image transmission apparatus 11 shown in FIG. 5 the object lens 42 and visual field are symmetrical and the viewing direction is parallel to the longitudinal axis of the image transmission apparatus 11 or of its shaft 20. The object lens 42 is optional.

Contrary to the image transmission apparatuses described above with reference to FIG. 1, the image transmission apparatus 11 shown in FIG. 5 comprises no lightwave conductors or other devices for transmitting illuminating light to the distal end 12 or for other type of illumination of an observed object. The shaft 20 of the image transmission apparatus 11 consequently can have a markedly smaller cross-section.

Figure 6:
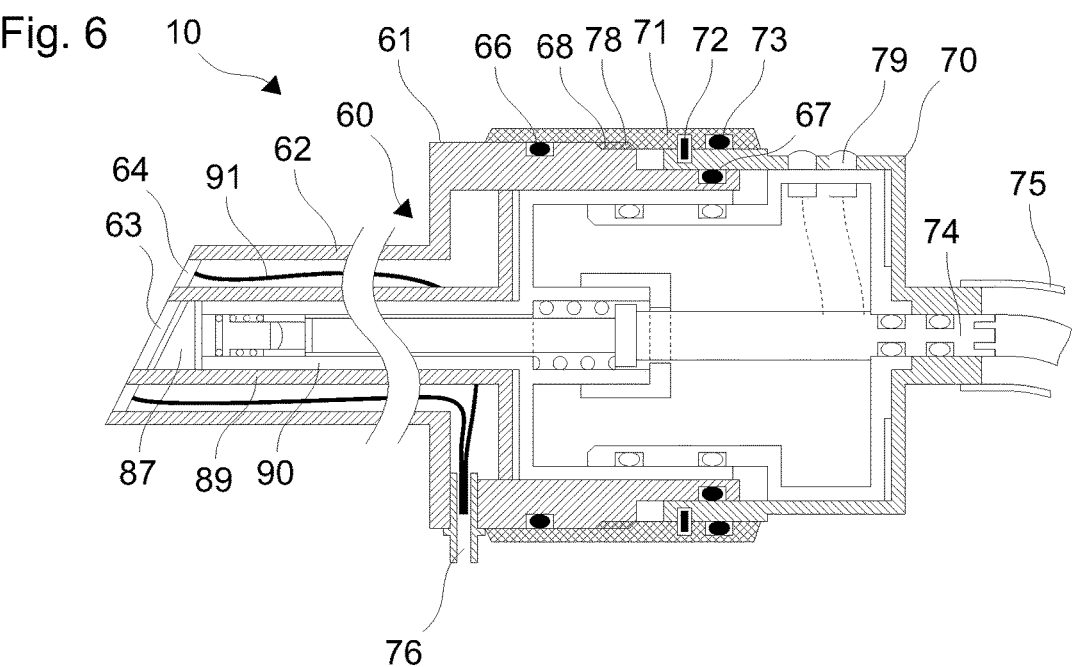
FIG. 6 is a schematic depiction of a visual field apparatus for an image transmission apparatus.

FIG. 6 shows a schematic depiction of a sleeve 60, consisting of a visual field apparatus 61 and a proximal sleeve part 70, for the image transmission apparatus 11 described above with reference to FIG. 5. The sleeve shown in FIG. 6 and in particular the visual field apparatus 61 resemble in a few particulars and characteristics the sleeves 60 and/or visual field apparatus 61 describe above with reference to FIG. 2. The visual field apparatus 61 shown in FIG. 6 is distinguished from the visual field apparatus described above with reference to FIG. 2, among other ways, by a guide tube 89 in the shaft 62. The lumen of the guide tube 89 forms a channel 90, which extends along the shaft 62 of the visual field apparatus 61 from the proximal end to the distal end of the shaft 62. The cross-section of the channel 90 is adapted to the shaft 20 of the image transmission apparatus 11, so that the shaft 20 of the image transmission apparatus 11, with little free play and friction, rotates around its longitudinal axis in the channel 90 and can be slid parallel to the longitudinal axis.

A prism 87 is positioned proximally from the observation window 63, similarly as with the sleeve described above with reference to FIG. 2. The material and geometry of the prism 87 cause the visual field, illuminated and recorded by the image transmission apparatus 11, to be asymmetrical with the longitudinal axis of the image transmission apparatus 11 or the viewing direction to be non-parallel to this longitudinal axis. Similarly as described above with reference to FIGS. 3 and 4, it is possible with one and the same image transmission apparatus 11, in combinations with different visual field apparatuses 61, to produce different viewing fields, which are distinguished with respect to their direction and size.

Outside the guide tube 89 but inside the shaft 62, lightwave conductors 91 run from an aperture or a junction 76 on the proximal end of the sleeve 60 all the way to a ring-shaped illuminating window 64, or to several such windows, on the distal end of the visual field apparatus 61. Instead of the illuminating window or windows 64 inserted as transparent components, the distal ends of the lightwave conductors 91 can simply be cemented in place on the distal end of the shaft 62 of the visual field apparatus 61 by means of an (optionally transparent) cement. By grinding and polishing the distal front surface of the shaft 62 with the ends of the lightwave conductors 48 and the cement, an optically high-caliber light outlet surface can be produced.

By means of a lightwave conductor cable that is not shown in FIG. 5 and is connected with the aperture or the junction 76, light can be conducted from an external light source by the lightwave conductors 91 to the distal end of the visual field apparatus 61 in order to illuminate there an object outside the sleeve 60. The arrangement of the illuminating window or windows 64 and of the distal ends of the lightwave conductors 91 causes the illuminated visual field to include the visual field recorded by the image transmission apparatus 11 or essentially to correspond to it.

Figure 7:
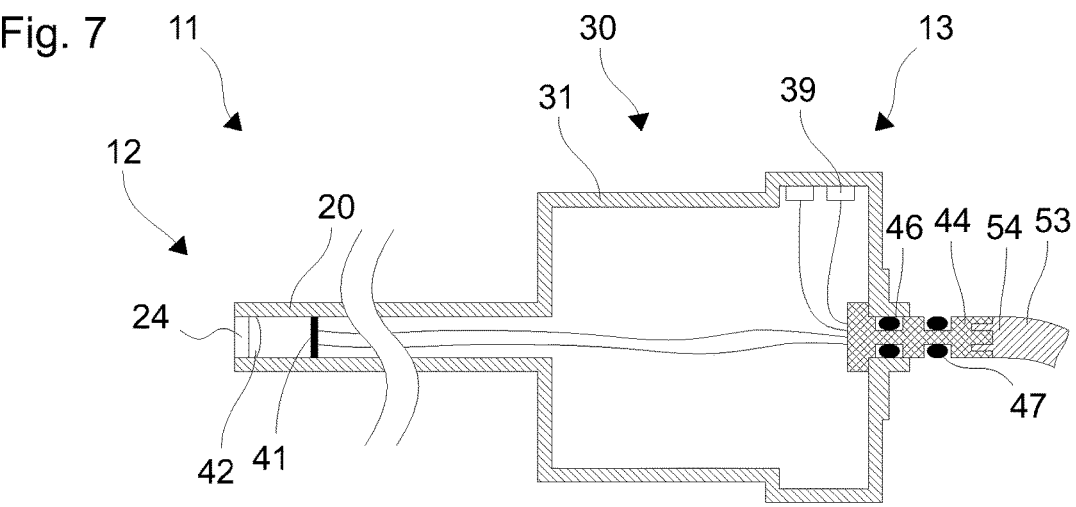
FIG. 7 is a schematic depiction of an image transmission apparatus.

FIG. 7 shows a schematic depiction of an image transmission apparatus 11 similar to the image transmission apparatus described above with reference to FIG. 5. Contrary to the image transmission apparatus described above with reference to FIG. 5, the image transmission apparatus 11 shown in FIG. 7 comprises no device for modifying the focus or varying the distance between the light-sensitive sensor 41 and the object lens 42. The object lens 42 is optional.

Figure 8:
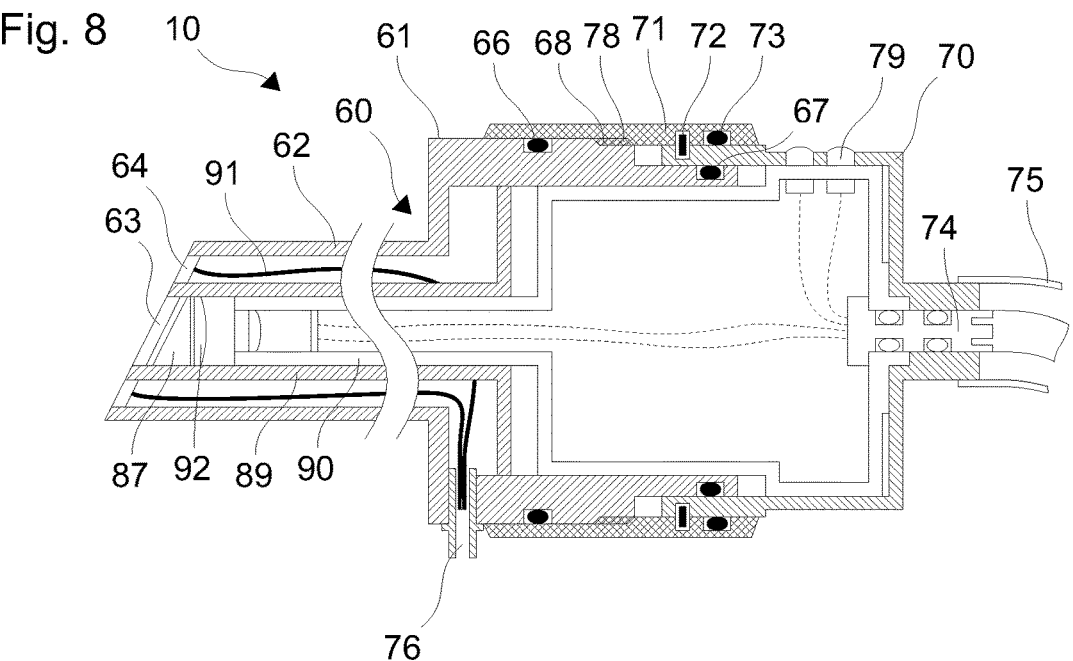
FIG. 8 is a schematic depiction of a visual field apparatus for an image transmission apparatus.

FIG. 8 shows a schematic depiction of a sleeve 60, consisting of a visual field apparatus 61 and a proximal sleeve part 70, for the image transmission apparatus 11 described above with reference to FIG. 7. The visual field apparatus 61 shown in FIG. 8 largely resembles the visual field apparatus described above with reference to FIG. 6. The visual field apparatus 61 shown in FIG. 8 comprises on its distal end a lens 92 in the observation beam path, which is not shown in the sleeves described above with reference to FIGS. 2 and 6 but which can optionally be provided as well.

As already described with reference to FIG. 2, it is also possible in the visual field apparatuses illustrated in FIGS. 6 and 8 to produce a relative axial sliding of the visual field apparatus 61 and of the proximal sleeve part 70 by rotating the sleeve 71 relative to the visual field apparatus 61. In the combination of the sleeve 60 with the image transmission apparatus 11 as shown in FIG. 8, a relative axial sliding of the visual field apparatus 61 and of the proximal sleeve part 70 produced in this way or otherwise causes a relative axial sliding of the image transmission apparatus 11 and of the visual field apparatus 61. The result, in particular, is a relative axial sliding of the light-sensitive sensor 41 and in some cases of the object lens 42 on the one hand and of the object lens 92 on the distal end of the visual field apparatus 61 on the other hand. This causes a modification in focusing or a sliding of the plane imaged by the object lens 92 on the visual field apparatus 61 and in some cases by the object lens 42 of the image transmission apparatus 11 sharply on the light-sensitive sensor 41.

Similarly as in the image transmission apparatuses described above with reference to FIGS. 1 and 5 and the visual field apparatuses described above with reference to FIGS. 2 and 6, a relative rotatability of the image transmission apparatus 11 and of the visual field apparatus 61 can also be provided in the image transmission apparatus 11 described with reference to FIG. 7 and the visual field apparatus 61 described with reference to FIG. 8. Thereby, as described above, rotation of the viewing direction of the endoscope 10 on a conical mantle can become possible without tipping of the image.

FIG. 9 shows a schematic depiction of an image transmission apparatus 11 similar to the image transmission apparatus presented above with reference to FIG. 7. The image transmission apparatus shown in FIG. 9 is distinguished from the image transmission apparatus described with reference to FIG. 7 by a somewhat different configuration of the handling device 30 with a groove on the proximal front side in which O-rings 94 are positioned. In addition, inside the handling device 30 a circuit board is shown with an analog and/or digital electronic switch, with which the magnetic field sensors 39 and the light-sensitive sensor 41 are coupled, and which, for example, is configured for signal preparation or signal processing.

FIG. 10 shows a schematic depiction of a visual field apparatus 61 similar to the visual field apparatus described above with reference to FIG. 8. The visual field apparatus 61 shown in FIG. 10, however, is configured and foreseen for use without a proximal sleeve part. Instead, the visual field apparatus 61 is configured to engage in the aforementioned proximal-front-side groove of the handling device 30 of the image transmission apparatus 11. O-rings 94 on the handling device 30 and on the visual field apparatus 61 are configured and positioned for fluid-tight insulation of the connection between the proximal end of the visual field apparatus 61 and the handling device 30 of the image transmission apparatus 11.

The visual field apparatus 61 shown in FIG. 10 comprises an eccentric arrangement of the guide tube 89 in the shaft 62. This results, among other things, in a correspondingly asymmetrical arrangement of the observation window 63 and of the illuminating window 64 as well as of the distal ends of the lightwave conductors 91. Proximally from the observation window 63, the visual field apparatus 61 comprises a prism 87, which diverts light impinging through the observation window 63 by total reflection on surfaces of the prism 87 to the object lens 92 and by means of this to the light-sensitive sensor 41 of the image transmission apparatus 11.

Also in the visual field apparatus shown in FIG. 10, instead of using illuminating windows 64 inserted as transparent components, the distal ends of the lightwave conductors 91 can simply be cemented in on the distal end of the shaft 62 of the visual field apparatus 61 by means of an (optionally transparent) cement. By grinding and polishing the distal front surface of the shaft 62 with the ends of the lightwave conductors 48 and the cement, an optically high-caliber light outlet surface can be produced.

On the proximal end of the object lens 92, a covering glass 93 is positioned that provides fluid-tight insulation from the channel 90 for the optical device with prism 87 and object lens 92 on the distal end of the visual field apparatus 61. The optical device with prism 87 and object lens 92 is thus completely encapsulated to be fluid-tight by the observation window 63 in the distal direction and by the covering glass 93 in the proximal direction. The visual field apparatus 61 can therefore be autoclaved without restriction, with no negative impact on the optical properties of the optical device on the distal end.

Similarly as the visual field apparatus 61 described above with reference to FIG. 10, so too the visual field apparatuses described above with reference to FIGS. 2, 6 and 8 can be configured contrary to the above illustration for use without a proximal sleeve part 70. To allow nevertheless for sterile enclosure or sheathing of the image transmission apparatus 11, a sterile cloth can be used. Said sterile cloth can be proximally connected with the visual field apparatus 61.

Each of the visual field apparatuses described with reference to FIGS. 2, 4, 6, 8 and 10 can be configured for different visual fields, in particular for different viewing directions and different sizes of the visual fields. As already mentioned, so too the image transmission apparatuses described with reference to FIGS. 5 through 10, similarly as described above with reference to FIGS. 3 and 4, can be combined with different visual field apparatuses to form endoscopes with varying visual fields.

Each of the image transmission apparatuses described above with reference to FIGS. 1, 3, 5 and 7 can comprise, in the handling device on the proximal end, one or more circuit boards with one or more analog or digital electronic switches for signal preparation or signal processing, as explained above in conjunction with FIG. 9.

As described above with reference to FIGS. 1 and 2, it is also possible with the visual field apparatuses presented above in conjunction with FIGS. 6, 8 and 10 to provide a common window or a one-piece transparent component in each case instead of the separate observation windows and illuminating windows. In this case, a light passes through said single window to illuminate an object in one direction and also reflected or scattered light goes from the illuminated object in the reverse direction.

Figure 11:
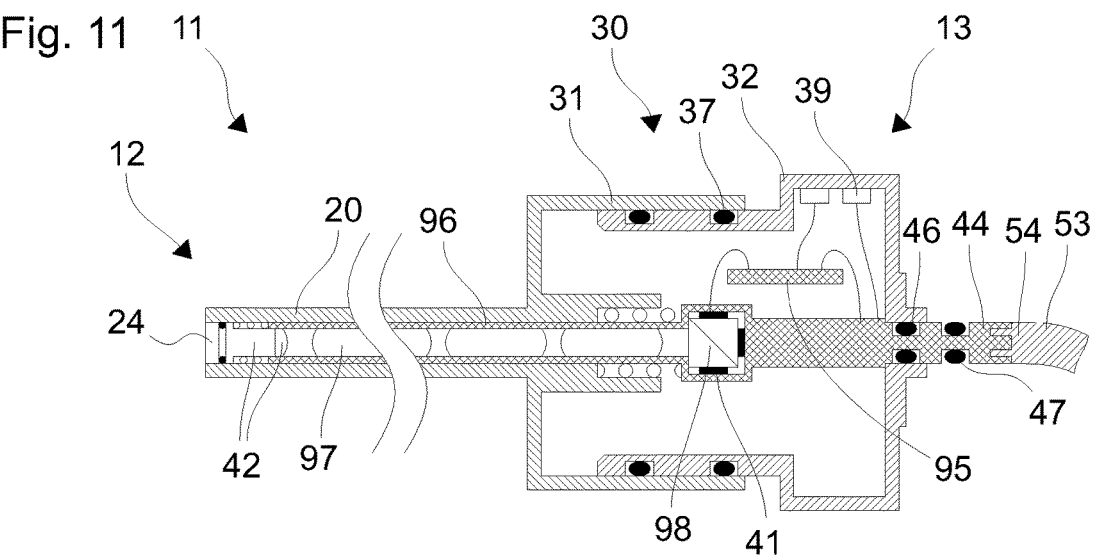
FIG. 11 is a schematic depiction of an image transmission apparatus.

FIG. 11 shows a variant on the image transmission apparatus 11 described above in conjunction with FIG. 5. The image transmission apparatus 11 shown in FIG. 11 comprises, instead of a sensor carrier 43, an optical carrier 96. The optical carrier 96, similarly as the sensor carrier of the image transmission apparatuses presented above, is pressed in proximal direction by a spring and supports itself on the proximal housing part 32 of the handling device 30. The optical carrier 96 is of tubular configuration in the shaft 20 of the image transmission apparatus 11 and contains an arrangement of rod lenses 97. The optical carrier bears a prism device 98 on the proximal end of the arrangement of the rod lenses 97 in the handling device 30, with several, in particular three, light-sensitive sensors 41. The three light-sensitive sensors 41 are coupled with an electronic switch on a circuit board 95.

Instead of the arrangement shown in FIG. 11 with three sensors 41 on a prism device 98, it is possible to provide a different number of sensors or just one sensor, which is sensitive to light with various wavelengths. CMOS or CCD sensors, for example, can be used as sensors. In addition, instead of one or more sensors, it is possible to provide an eyepiece for direct observation by the human eye or a coupling for connecting a video camera on the proximal end of the image transmission apparatus 11.

The object lens 42 is fastened on the distal end of the shaft 20 of the image transmission apparatus 30 and thus has an unchangeable position relative to the distal housing part 31 of the handling device 30. The rod lenses 97, prism arrangement 98 and light-sensitive sensors 41 are fastened on the optical carrier 81, which supports itself on the proximal housing part 32 of the handling device 30. The rod lenses 97, prism arrangement 98 and light-sensitive sensors 41 therefore are at an unchangeable position relative to the proximal housing part 32 of the handling device 30. A relative sliding of the proximal housing part 32 and of the distal housing part 31 of the handling device 30 thus causes a relative sliding of the object lens 42 on the one hand with respect to the arrangement of rod lenses 97, of the prism device 98 and light-sensitive sensors 41 on the other hand.

Light entering through the observation window 24 into the image transmission apparatus 11 is transmitted from the object lens 42 and the arrangement of rod lenses 97 to the proximal end 13 of the image transmission apparatus 13, split up by the prism device 98 into several wavelength ranges, and depending on the wavelength is imaged onto one (or more) of the sensors 41. The light-sensitive sensors convert the light into electric signals, which are prepared and processed, in particular reinforced and digitized, by the electronic switch on the circuit board 95.

Figure 12:
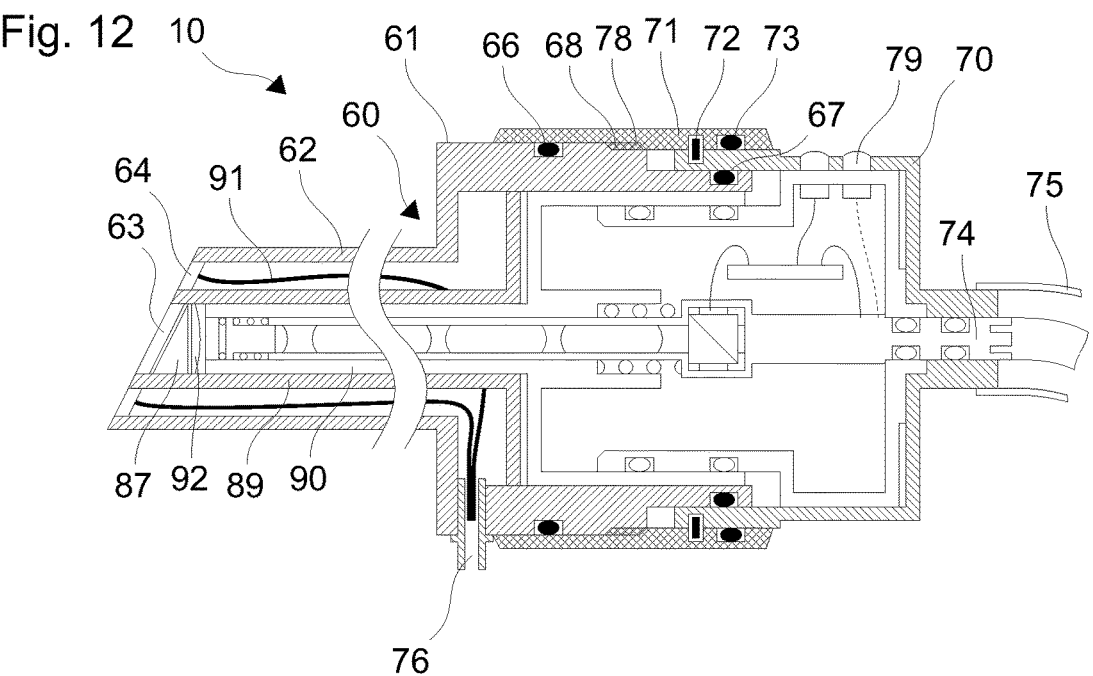
FIG. 12 is a schematic depiction of a visual field apparatus for an image transmission apparatus.

FIG. 12 shows a sleeve 60 with a visual field apparatus 61 that forms a distal sleeve part, and with a proximal sleeve part 70 similar to the visual field apparatus described above in conjunction with FIG. 8. The visual field apparatus shown in FIG. 12, however, is configured in such a way that the distal housing part 31 of the handling device 30 and the shaft 20 are slidable with respect to the visual field apparatus 61. Thus, both the object lens 42 of the image transmission apparatus 11 on the one hand and the arrangement of rod lenses 97, prism device 98 and light-sensitive sensors 41 on the other hand are moveable independently of one another relative to the object lens 92 on the distal end of the visual field apparatus 61. Thus, with corresponding configuration of the object lens 92 on the distal end of the visual field apparatus 61, of the object lens 42 on the distal end of the image transmission apparatus 11, of the arrangement of rod lenses 97, of the prism device 98 and of the light-sensitive sensors 41, it becomes possible both to displace the focal length and/or to displace the size of the visual field as well as to focus or displace the surface sharply imaged on the light-sensitive sensors 41.

The described displacement of the focal length and focus is possible not only with the image transmission apparatus 11 described above with reference to FIG. 11 but also, for example, in combining the image transmission apparatus 11 presented above with reference to FIG. 5 with one of the visual field apparatuses described above in conjunction with FIGS. 8 and 12. In addition, it is possible to displace the focal length and focus by combining the image transmission apparatus presented above with reference to FIG. 1 with the visual field apparatus presented above in conjunction with FIG. 2 if the latter, contrary to the depiction in FIG. 2, comprises an object lens or lens on the distal end.

The described displacement of the focal length and focus requires, as mentioned, an independent sliding of the distal housing part 31 of the handling device 30 of the image transmission apparatus 11 with the shaft 20 on the one hand and of the proximal housing part of the handling device 30 on the other hand with respect to the visual field apparatus 61. For this purpose, the housing parts 31, 32 of the handling device, the visual field apparatus 61 and the proximal sleeve part 70, for example, contrary to the depiction in FIG. 12 are configured in such a way that an axial sliding of the proximal sleeve part 70 with respect to the visual field apparatus 61 causes a displacement of the focal length and a rotation of the proximal sleeve part 70 with respect to the visual field apparatus 61 causes a displacement of the focus.

With visual field apparatuses 61 and image transmission apparatuses 11, as presented above with reference to FIGS. 1 through 12—as already mentioned—the visual field can be modified by exchanging the visual field apparatus 61. If the viewing direction is not parallel to the longitudinal axis of the visual field apparatus 61 and of the image transmission apparatus 11, the viewing direction can be rotated on a conical mantle by rotating the visual field apparatus 61 around the longitudinal axis. In a few embodiments, the visual field apparatus 61 and image transmission apparatus 11 can be rotated independently of one another. In this case, by turning the image transmission apparatus 11, the image recorded by a video camera can be turned, in particular set upright. The video camera here can be positioned on the distal or proximal end of the image transmission apparatus 11 or can be coupled with the proximal end of the image transmission apparatus. For example, in the embodiments presented above with reference to FIGS. 1 and 2, 5 and 6, 11 and 12, the recorded image, rather than by a rotation of the entire image transmission apparatus 11, can be rotated by a rotation merely of the sensor carrier 43 or of the optical carrier 96 or of the prism device 98.

Alternatively or simultaneously, the visual field apparatus 61 and the image transmission apparatus 11 can be configured in such a way that a rotation of the two relative to one another causes an axial sliding of one or more lenses. For this purpose, a thread, a helical groove or a helical stud, for example, is provided on the visual field apparatus 61 and an axial groove or axial stud on the image transmission apparatus 11. A frame of the lens or lenses is engaged both with the thread, helical groove or helical stud on the visual field apparatus 61 and with the axial groove or axial stud on the image transmission apparatus 11. Alternatively, the thread, the helical groove and/or helical stud are provided on the image transmission apparatus 11 and the axial groove and/or axial stud on the visual field apparatus 1. It is also possible to have two threads or helical structures with opposite thread directions.

In the described cases, a relative rotation of the visual field apparatus 61 and of the image transmission apparatus 11 can cause an axial movement of the lens or lenses. Because of the axial movement of the lens or lenses, the focus and/or focal length and thus the size of the visual field can be modified.

Alternatively or simultaneously—as already described in part—a simple axial relative movement of the visual field apparatus 61 and image transmission apparatus 11 can cause a modification of the focus and/or focal length or the visual field. For this purpose, because of the relative movement, one or more lenses or a rod lens system or light-sensitive sensor can be slid relative to one another and/or to the object. The relative movement, for example—as already indicated—is generated by a rotation of the rotatable sleeve 71, which is connected so that it can rotate, but not axially slide, with the proximal sleeve part 70. Reciprocally engaging threads 68, 78 on the visual field apparatus 61 or on the rotatable sleeve 71 can cause a rotation of the rotatable sleeve 71 relative to the visual field apparatus 61 into an axial sliding of the visual field apparatus 61 relative to the proximal sleeve 71, and here the image transmission apparatus 11 is connected in friction-locked or form-fitted manner with the proximal sleeve 71.

Figure 13:
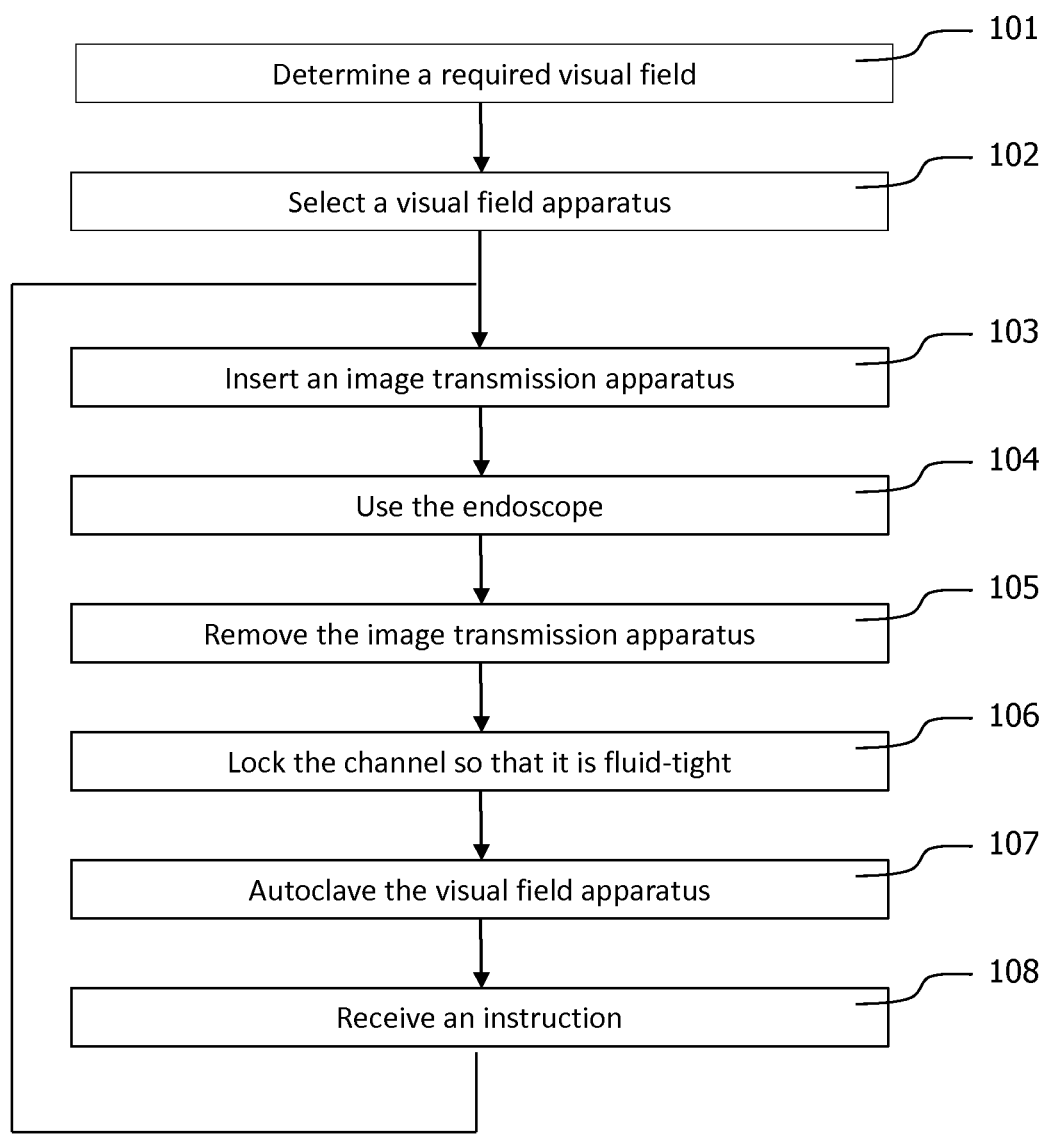
FIG. 13 is a schematic flow diagram for a method for providing and autoclaving an endoscope.

FIG. 13 shows a schematic flow diagram of a method for providing an endoscope and for autoclaving a visual field apparatus. Although this method can also be executed with image transmission apparatuses—in particular, endoscopes—and visual field apparatuses, which differ from those presented above with reference to FIGS. 1 through 12, hereinafter reference numbers from FIGS. 1 through 12 are used in order to facilitate understanding of the method.

In a first step 101, a visual field required in a successive application is determined. In a second step 102, a visual field apparatus 61 is selected with the determined visual field 90. In a third step 103, an image transmission apparatus 11 is combined or conducted together with the selected visual field apparatus 61, in particular inserted into the channel 90 of the selected visual field apparatus 61, in order to form an endoscope 10.

The first step 101, second step 102 and third step 103 form a method for providing an endoscope for a successive application of the endoscope, for example in a medical investigation or a medical procedure.

In a fourth step 104, the endoscope provided by the first step 101, second step 102 and third step 103 is used. After use of the endoscope 10, in a fifth step 105 the image transmission apparatus 11 is removed from the visual field apparatus 61.

After removal of the image transmission apparatus 11 in the fifth step 105, in a sixth step 106 the channel 90 on the proximal end is closed in fluid-tight manner, for example by means of an insulating plug. In a seventh step 107, the visual field apparatus 61 with the closed channel 90 is autoclaved. After autoclaving, in an eighth step 108 the channel 90 is opened. The sixth step 106 and eighth step 108 are not required when the optical apparatus on the distal end of the visual field apparatus, for example, as described above with reference to FIG. 10, is completely encapsulated or closed in fluid-tight manner in both the distal and proximal directions.

The sixth step 106, seventh step 107 and eighth step 108 form a method for autoclaving the visual field apparatus. After autoclaving the visual field apparatus, an image transmission apparatus 11 can again be inserted into the visual field apparatus 61 in order to repeat the third step 103 and the following steps.

What is claimed is:

1. An endoscope, comprising:
a visual field apparatus having a channel extending in a direction between a proximal end and a distal end of the visual field apparatus, and an optical device disposed relative to a distal end of the channel and closed within the channel in a fluid-tight manner; and
an image transmission apparatus having a shaft at least partially received within the channel of the visual field apparatus, a handling device connected to a proximal end of the shaft, and at least one of (i) a device configured to optically transmit an image from a distal end of the shaft to the proximal end of the shaft, and (ii) a light-sensitive sensor configured to convert an image into an image signal;
wherein the proximal end of the visual field apparatus is mechanically connected to the handling device of the image transmission apparatus such that a fluid-tight connection is defined therebetween; and
wherein the proximal end of the visual field apparatus includes an operating element positioned opposite a sensor on the handling device of the image transmission apparatus, wherein actuation of the operating element actuates the sensor to control a function of the image transmission apparatus.

2. The endoscope of claim 1, wherein the optical device is configured to at least one of refract light, reflect light, and bend light.

3. The endoscope of claim 1, wherein the optical device includes at least one of a prism, a mirror, and a lens.

4. The endoscope of claim 1, further comprising an adjustment device configured to selectively adjust a position of the image transmission apparatus in a longitudinal direction in the channel.

5. The endoscope of claim 1, further comprising:
a lightwave conductor configured to transmit illuminating light from the proximal end of the visual field apparatus to the distal end of the visual field apparatus to illuminate an object that is to be observed.

6. The endoscope of claim 1, further comprising:
a light outlet device disposed relative to the distal end of the visual field apparatus, the light outlet device configured to conduct illuminating light into an area outside the visual field apparatus.

7. The endoscope of claim 1, further comprising:
a fluid-tight inserted transparent closing disposed relative to the distal end of the shaft.

8. The endoscope of claim 1, wherein the image transmission apparatus is configured to generate a sharp image of an object when the shaft of the image transmission apparatus is at least partially received within the channel of the visual field apparatus; and
wherein the optical device is configured to influence at least one of a visual field and a focusing of the image transmission apparatus.

9. The endoscope of claim 1, wherein the shaft of the image transmission apparatus is removable from the channel of the visual field apparatus.

10. The endoscope of claim 1, wherein the image transmission apparatus extends along a longitudinal axis between a proximal end and a distal end thereof; and
wherein the shaft is received at least partially within the channel of the visual field apparatus in a manner that permits rotation of the shaft about the longitudinal axis and relative to the channel.

11. An endoscope, comprising:
a visual field apparatus having a channel extending in a direction between a proximal end and a distal end of the visual field apparatus, and an optical device disposed relative to a distal end of the channel and closed within the channel in a fluid-tight manner; and
an image transmission apparatus having a shaft at least partially received within the channel of the visual field apparatus, a handling device connected to a proximal end of the shaft, and at least one of (i) a device configured to optically transmit an image from a distal end of the shaft to the proximal end of the shaft, and (ii) a light-sensitive sensor configured to convert an image into an image signal;

wherein the proximal end of the visual field apparatus is mechanically connected to the handling device of the image transmission apparatus such that a fluid-tight connection is defined therebetween;
wherein the image transmission apparatus is selectively moveable relative to the optical device of the visual field apparatus, or vice versa, in a direction of a longitudinal axis of the image transmission apparatus;
wherien the visual field apparatus includes a first sleeve disposed relative to the handing device of the image transmission apparatus;
wherein the visual field apparatus is configured such that rotation of the first sleeve relative to the handling device and about the longitudinal axis of the image transmission apparatus causes relative movement between the visual field apparatus and the image transmission apparatus in the direction of the longitudinal axis;
wherein the visual field apparatus includes a second sleeve, and the distal end of the channel is disposed at least partially within the second sleeve; and
wherein the first sleeve is selectively rotatable relative to the second sleeve, or vice versa.

12. The endoscope of claim 11, wherein the image transmission apparatus includes a light-sensitive sensor configured to convert an image into an image signal; and
wherein the visual field apparatus and the image transmission apparatus are configured such that relative movement therebetween in the direction of the longitudinal axis of the image transmission apparatus causes a change in at least one of a focus, a focal length, and a visual field.

13. The endoscope of claim 11, wherein the channel of the visual field apparatus extends in a direction of, and is concentrically aligned about, a longtiduinal axis of the image transmission apparatus; and
wherein the visual field apparatus is configured such that the first sleeve is selectively rotatable relative to the channel and about the longitudinal axis of the image transmission apparatus.

* * * * *